United States Patent
Hoang et al.

(10) Patent No.: US 6,723,689 B1
(45) Date of Patent: Apr. 20, 2004

(54) EMOLLIENT ALCOHOL SKIN DISINFECTING FORMULATION

(75) Inventors: Minh Quang Hoang, Taylorsville, UT (US); Donald Edward Hunt, Provo, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 15 days.

(21) Appl. No.: 10/338,457

(22) Filed: Jan. 8, 2003

(51) Int. Cl.[7] .............................. C11D 1/62; C11D 3/22; C11D 3/37; A61K 7/00
(52) U.S. Cl. ..................... 510/130; 510/101; 510/131; 510/138; 510/159; 510/383; 510/384; 510/386; 510/391; 510/419; 424/404; 424/70.28; 424/78.07
(58) Field of Search ................................ 510/101, 130, 510/131, 138, 159, 383, 384, 386, 391, 419; 424/404, 70.28, 78.07

(56) References Cited

U.S. PATENT DOCUMENTS 6,136,771 A * 10/2000 Taylor et al. ............... 510/388

* cited by examiner

Primary Examiner—Brian P. Mruk
(74) Attorney, Agent, or Firm—James J. Murtha

(57) ABSTRACT

An antimicrobial composition comprising an alcohol in an amount from about 60 to about 95 weight percent of the total composition, a preservative, a cationic cellulose polymer thickening agent, a moisturizer and/or, a cationic emulsifier, and water in an amount from about 6 to about 30 weight percent. The skin disinfecting formulation will not irritate, dry or crack the skin and will provide antimicrobial effectiveness to the skin.

26 Claims, No Drawings

EMOLLIENT ALCOHOL SKIN DISINFECTING FORMULATION

BACKGROUND OF THE INVENTION

1. Field of the Invention

The present invention relates to an antimicrobial composition for use as an emollient alcohol based skin disinfectant that will not irritate or dry the skin. The skin disinfecting formulations of the present invention arc particularly useful in the healthcare profession as a hand healthcare preparation or as a pre-surgical scrub without requiring a secondary emollient application.

2. Description of Relevant Art

Hand washing by healthcare professionals is an essential component of infection control activities. Healthcare professionals attending to patient care wash their hands to control the spread of infection from patient to patient and surgical procedures are routinely proceeded by surgical hand scrubbing and patient pre-operative skin preparation.

Hand washing procedures are performed in several ways. Several procedures include an ordinary antimicrobial bar soap, a skin disinfecting alcohol based preoperative preparation agent, or rubbing alcohol. The repeated use of these procedures causes the hands to become rough, dry and cracked.

The majority of the commercially available scrubs include detergents and an antimicrobial agent or a preservative. Examples of the antimicrobial or preservative agents include iodine formulations, iodophors, phenolic compounds such as parachlorometaxylenol and hexachlorophene and bis-biguanides such as chlorhexidine gluconate (CHG).

Although alcohol in general is recognized for its very effective disinfecting properties, it is not used directly with skin or in scrub formulations because it is a defatting agent. When alcohol is applied to the human skin, it makes it very dry, often developing chapped and cracked skin. Furthermore, it is difficult to formulate a detergent solution with alcohol that will lather like ordinary soaps and detergents when used with water. However, due to the disinfecting properties of alcohol, it is desirable to produce a skin disinfecting formulation with alcohol which is mild and gentle to the skin, and is effective at controlling microorganism populations on the skin.

SUMMARY OF THE INVENTION

The present invention is a skin disinfecting formulation that provides antimicrobial effectiveness and is mild and gentle to human skin. The skin disinfecting formulation desirably comprises an alcohol, a thickening agent, a preservative, an emulsifier, a moisturizer and/or emollient and water. The disinfecting formulation is used in a method of disinfecting a substrate comprising the step of applying an effective amount of the disinfecting formulation to the substrate, such as a hand. Additionally, an antimicrobial formulation of alcohol or a solution of chlorhexidine gluconate may be applied to the substrate.

Preferably, the skin disinfecting formulation may further comprise a colorant or a fragrance. Most preferably, the skin disinfecting formulations comprise by weight:

(a) from about 60% to about 95% of an alcohol;
(b) from about 0% to about 3%, preferably from about 0.01 to about 3.0%, of a thickening agent;
(c) from about 1% to about 5%, preferably from about 0.01 to about 3.0%, of a cationic emulsifier;
(c) from about 0% to about 5%, preferably from about 0.001 to about 5.0%, of a preservative/antimicrobial agent;
(d) from about 0.05% to about 5% of a fragrance;
(e) from about 0.05% to about 1% of a colorant; and
(j) from about 6% to about 30% of water.

The skin disinfecting formulations of the present invention are useful in providing substantial antimicrobial effectiveness and surprisingly, provide substantial non-irritancy to the skin view of the alcohol component of the formulations.

Another attribute of the skin disinfecting formulation is its ability to not dry the skin.

Another advantage of the skin disinfecting formulation is the compatibility with other Chlorohexidine Gluconate products, which enhances the antimicrobial activity of both formulations by further reducing the microbial flora on the substrate.

A further advantage of the skin disinfecting formulations of the present invention is the potential to provide long-term residual activity on the applicant's skin to prevent bacteria growth back to the base line of normal skin flora population.

The skin disinfecting formulations of the present invention will disinfect the skin while also providing emolliency to the skin. Further, the skin disinfecting formulations of the present invention can also be used as a general purpose hand wash to decontaminate the hands of healthcare professionals before examining any patient.

Healthcare professionals perform a routine hand scrubbing procedure many times a day. The typical and/or commonly used scrub solutions contain chemical compounds such as iodine, chlorhexidine gluconate (CHG), PCMX and hexachlorophenc. All of these chemical compounds disinfect the skin as well as bind to the skin, thus providing persistent activity. Healthcare professionals may also use the skin disinfecting formulation of the present invention throughout the day. Since health care professionals scrub and wash their hands many times a day, the chemical compounds may buildup on their skin and accumulate through out the day. The intended use of the present invention includes rinsing off the hands and forearms with water to remove any residual chemical build up. Therefore the skin disinfecting formulation of the present invention would be ideal for both routine use throughout the day and as a final wash before leaving the work place.

Surprisingly, the formulations of the present invention provide substantially effective skin disinfecting properties with the use of alcohol in the formulations as well as being mild and gentle to the skin, and substantially effective against microorganisms. Antimicrobial formulations of the present invention are typically packaged in a container. Typically, a foot pump is used to create an increased pressure inside the closed container. The positive pressure difference across the container wall results in the solution being forced up a solution delivery straw. Such a formula must therefore satisfy certain physical requirements, which include: viscosity in the range of 100–2500 cps; alcohol as an active ingredient in the range of 60–95% w/w; and antimicrobial agents in a preservative range of 0.001–5.0% w/w. In addition, the formulation must be efficacious and non-irritating when used. With these parameters in mind the present invention provides an alcohol scrub with greater than 60% alcohol that is effective against microorganisms and causes rapid bacterial reduction.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The skin disinfecting formulation of the present invention comprises an alcohol, a thickening agent, an emulsifier, a preservative, a moisturizer and/or emollient and water. The skin disinfecting formulations may further comprise a fragrance and/or a colorant.

An alcohol is preferably used in the skin disinfecting formulations because of the inherent bactericidal properties. Generally, a concentration of alcohol over 60% is an effective germicidal agent. It kills gram-positive, gram-negative bacteria, fungi, mold and a variety of viruses. The potent activity of alcohol against micro-organisms is due to its denaturation of proteins and enzymes and cellular dehydration. Typically, the more concentrated the alcohol solution the more potent the antimicrobial effect. However, increasing the alcohol concentration has the deleterious effect of increasing the level of skin irritancy on healthcare workers using the solution. Surprisingly, the present invention describes a formulation with an alcohol concentration of 70% without an increase in skin irritancy.

An alcohol for use in the skin disinfecting formulation includes, but is not limited to, isopropyl alcohol, ethanol and n-propyl alcohol.

The preferred alcohol for use in the skin disinfecting formulations is isopropanol and ethanol. Preferably, ethyl alcohol may be present in the skin disinfecting formulation in an amount from about 60 to about 95 weight percent, and most preferably at about 70 weight percent.

Thickening agents are used in the skin disinfecting formulations to adjust the viscosity and stability of the formulations. Generally, due to the use of alcohol as a solvent, the typical thickening agent of the present invention remains soluble in alcohol concentrations up to at least 70%. The thickening agents used in the present invention are cationic polymers. Typical cationic thickening agents include cellulosic materials such as starch, methocel (methyl cellulose ethers) and hydroxycellulose.

It is believed that hydrophobic thickeners provide cellulose compositions that improve the biocidal activity of the composition due to the minimum amount of water absorbed from the composition during the thickening process. Thickeners that are less hydrophobic may cause the skin disinfecting formulations to be turbid or milky because the skin disinfecting formulations may precipitate if there is not sufficient water in the composition.

A suitable thickening agent, for skin disinfecting formulations is hydroxypropyl methylcellulose, METHOCEL® (a trademark of the Dow Chemical Company, Midland, Mich.) sold by The Dow Chemical Company. METHOCEL® thickener is 91% hydroxypropyl methyl cellulose which dissolves in aqueous alcohol solution, is nonionic, and is a highly efficient water retention agent.

Preferably, the thickening agent may be present in the skin disinfecting formulations in an amount from about 0 to about 3 weight percent and most preferably at about 1 weight percent.

An emulsifier is typically used in the skin disinfecting formulations to disperse oily emollients in water solution. More importantly, an emulsifier is a solubilizer. A preferred cationic emulsifier is a cationic quaternary ammonium salt.

A suitable cationic emulsifier for the skin disinfecting formulation is Incroquat Behenyl® (Trademark of Croda, Inc., Parsippany, N.J.) sold by Croda, Inc. Incroquat Behenyl® is a compound of 25% active solution of behenyl trimonium methosulfate in cetearyl alcohol and is available in flaked/pastel form. This cationic polymer is a very active conditioning agent and bonds to skin through the native negative charge on the skin.

A second suitable emulsifier available from Croda, Inc. is Incroquat CR Concentrate, which consists of cetearyl alcohol, PEG-40 Castor Oil, and stearalkonium chloride. The Incroquat CR Concentrate is one part formulating aid and one part conditioner and self emulsifier. Incroquat CR concentrate will produce a creamy feel, while rinsing and conditioning efficiently.

A combination of these two cationic emulsifers is preferred. The combination provides a smooth after feel and neutralizes the static charge of the skin especially when used in conjunction with isopropyl palmitate, or Incroquat B65C® or Incroquat CT30®, all available from Croda, Inc.

Alcohol is an excellent antimicrobial agent and will preserve the skin disinfecting formulation very well. However, when the formulation is applied to the skin, the alcohol will evaporate after a period of time. Thus, a small amount of a non-volatile organic antimicrobial agent may be added to the skin disinfecting formulation to preserve the antimicrobial effect of the formulation for an extended period of time.

The preservative is selected so as not to upset desirable physical and chemical properties of human skin. A properly selected preservative maintains stability under use and storage conditions (pH, temperature, light, etc.), for a required length of time. It will also prevent the growth of microbes and/or is effective in killing microbes to achieve a continuing antimicrobial effect.

A suitable preservative may be selected from the class of phenolics such as parachlorometaxylenol or phenoxy ethanol, or bis-biguanides such as CHG, chlorhexidine diacetate or Quaterium class such as Benzethonium chloride, benzalkonium chloride. Hexetidine, Germaben II®, Kathon CG®, Triclosan are other antimicrobial agents that may also be suitable as preservatives. Benzethonium chloride and benzalkonium chloride as fIlyamine 3500 a trademark of Lonza, Inc., (Fair Lawn, N.J.) available from Lonza, Inc., CHG is available from Xttrium laboratories, (Chicago, Ill.) and Germaben II is available from Sutton Laboratories, (Chatham, N.J.). Two other preservatives popular in the cosmetics industry are methylparaben and propylparaben. These chemicals are available from Mallinckrodt Chemical Company (St.Louis, Mo.). A preferred preservative includes a mixture of benzethonium chloride in an amount from about 0.02 to about 1.0 percent by weight, benzalkonium chloride in an amount from about 0.02 to about 1.0 percent by weight, and chlorhexidine gluconate. in an amount from about 0.01 to about 2.0 percent by weight.

Preferably, the preservative may be present in the skin disinfecting formulations in an amount from about 0 to about 5 weight percent and most preferably at about 0.5 weight percent. In an even more preferred embodiment combinations of two or more preservative compounds are present in the formulation.

Emollients in their physical form are thin liquids, oils of various viscosities, fatty solids or waxes. Hydrocarbons function essentially as emollients by virtue of their ability to lubricate and/or hold water at the skin surface due to their relative occlusivity. Mineral oil is such a fluid. Some emollients are hydrophilic (glycerin, propylene glycol) and are water soluble lubricants and humectants. Since emollients may be fatty chemicals, oily or waxy in nature, they can impart barrier properties to formulations and are then referred to as moisturizers.

Moisturizers are substances which provide external lubricant behavior, such as to soften and soothe the skin because they encourage skin water retention.

The function of the moisturizer and/or emollient in the skin disinfecting formulation is to provide relief for dry and sensitive skin. Therefore, chapping of the skin may be prevented. In addition, the moisturizer and/or emollient does not leave a tacky after feel on the skin. The moisturizer and/or emollient is present in the composition in an amount from about 0.005 to about 5.0 weight percent of the total composition.

Suitable moisturizers and/or emollients in the skin disinfecting formulations include isopropyl palmitate, lanolin, derivatives of lanolin such as the ethoxylated acetylated alcohol and surface active alcohol derivatives of lanolin, propylene glycol, polypropylene glycol, polyethylene glycol, mineral oils, squalane, fatty alcohols, glycerin, and silicons such as dimethicone, cyclomethicone, simethicone. Preferred moisturizers and/or emollients are selected from lanolin derivatives, polyols and cetylethers. Most preferably, the moisturizer and/or emollient in the skin disinfecting formulations is a combination of mineral oil, dimethicone, glycerine, isopropyl palmitate.

Preferably, moisturizers and/or emollients are present in the skin disinfecting formulations in an amount from about 0.05 to about 5 weight percent and most preferably at about 1.0 weight percent.

Other ingredients which are conventional or desirable for aesthetic purposes may also be added to the skin disinfecting formulations as long as they do not adversely affect the overall properties of the formulation. Such ingredients may include a perfume or fragrance to provide a pleasing scent or a dye to provide a characteristic color. The composition additionally contains an effective amount, preferably about 0.05 to about 0.5% by weight, of diazolidinyl urea and 3-Iodo-propynylbutylcarbamate. Also preferred is a composition that contains a total amount of diazolidinyl urea, methyl paraben, propyl paraben, and propylene glycol in an amount from about 0.05 to about 2.0 percent by weight.

The skin disinfecting formulations of the invention may be prepared in 4 individual Steps and in three separate vessels. Step 1 involves the mixing of the alcohol, water, and thickening agent. The thickening agent (Methocel Cellulose) is dispersed in the alcohol/water mixture at ambient temperatures. The subsequent mixture is agitated until the thickening agent is fully dissolved and no granulation remains. In step 2, a separate container is used which is suitable for heating the various emulsifiers and moisturizing agents. The emulsifier mixture may include one or more of the following methylparaben, propylparaben, isopropyl palmitate, mineral oil, incroquat CR, dimethicone-350, and Incroquat BTMS. The emulsifying agents are heated to 60–85° C. with mixing until all the ingredients are melted and thoroughly mixed. In Step 3 a vessel of water and glycerin is heated to 50–80° C. with mixing. The heated ingredients from Step 2 and any fragrance or colorant is then added with vigorous mixing to the glycerin/water solution of Step 3. The water/glycerin/emulsifier solution is then cooled to below 35° C. with continued mixing. Finally, in Step 4 the water/glycerin/emulsifier mixture in Step 3 is added to the alcohol/water/thickening agent mixture in Step 1 and mixed thoroughly. Preservatives are then added to the solution including one or more of the following: benzethonium chloride; benzalkonium chloride; and CHG. The solution is mixed continuously until a homogenous mixture is achieved.

BIOCOMPATIBILITY

The skin disinfecting formulations of the present invention were prepared with the ingredients as shown in Table I. The formulations were mixed in the manner described above. In each formulation, ethyl alcohol was used as the primary antimicrobial agent. Additional preservatives include benzethonium chloride, benzalkonium chloride, and CHG.

TABLE I

Antimicobial Formulation Compositions for the present invention
Compositions are listed weight/100 weight solution

| Ingredient | Formula A | Formula B | Formula C | Formula D | Formula E | Formula F | Formula G | Formula H |
|---|---|---|---|---|---|---|---|---|
| Ethyl alcohol | 72.188 | 72.188 | 76.500 | 72.188 | 72.188 | 72.188 | 72.188 | 72.188 |
| Cellulose (Methocel) | 1.005 | 1.005 | 1.000 | 1.005 | 1.005 | 1.005 | 1.005 | 1.005 |
| Incroquat BTMS | 0.100 | 0.100 | 0.200 | 0.200 | 0.200 | 0.200 | 0.200 | 0.200 |
| Mineral Oil | | | 0.0100 | 0.0100 | 0.100 | | 0.100 | 0.100 |
| Dimethicone 350 | | 0.010 | 0.015 | 0.015 | 0.015 | 0.015 | 0.015 | 0.015 |
| Benzethonium Chloride | 0.099 | 0.099 | 0.099 | 0.099 | 0.099 | 0.099 | 0.099 | 0.099 |
| Incroquat CR | 0.051 | 0.050 | 0.050 | 0.050 | | | 0.050 | 0.050 |
| Benzalkonium Chloride | 0.099 | 0.099 | 0.099 | 0.099 | 0.099 | 0.099 | 0.099 | 0.099 |
| Glycerin | 0.708 | 0.700 | 0.700 | 0.700 | 0.000 | 0.000 | 0.700 | 0.700 |
| Germaben II | 0.030 | | 0.030 | 0.030 | 0.030 | 0.030 | 0.030 | 0.030 |
| Purified Water | 25.196 | 25.458 | 20.905 | 25.223 | 25.423 | 25.298 | 25.141 | 25.223 |
| CHG (20% Solution) | 0.090 | 0.090 | 0.090 | 0.090 | 0.090 | 0.090 | 0.090 | 0.090 |
| Isopropyl Palmitate | 0.202 | 0.200 | 0.200 | 0.200 | 0.200 | 0.200 | 0.200 | 0.200 |
| Fragrance | 0.030 | | 0.030 | | | | | |
| Hexetidine | | 0.002 | | 0.002 | 0.002 | 0.002 | | 0.002 |

TABLE I-continued

Antimicobial Formulation Compositions for the present invention
Compositions are listed weight/100 weight solution

| Ingredient | Formula A | Formula B | Formula C | Formula D | Formula E | Formula F | Formula G | Formula H |
|---|---|---|---|---|---|---|---|---|
| lincroquat B65C | | | | | 0.050 | 0.050 | | |
| Propylene Glycol | | | | | 0.500 | 0.700 | | |
| Triclosan | | | | | | | 0.002 | |
| Petrolatum | 0.202 | | | | | | | |
| Incroquat CTC30 | | | | | | | 0.100 | |
| Squalane | | | | | | 0.025 | | |
| Total | 100.000 | 100.000 | 100.000 | 100.000 | 100.000 | 100.000 | 100.000 | 100.000 |

Formula C of the present invention was tested for primary dermal irritation and skin sensitization, based upon procedures described in ISO 10993–10: 1995 Standard, "Biological Evaluation of Medical Devices, Part 10-Tests for Irritation and Sensitization." Ten test guinea pigs were patched with the test article and five guinea pigs were patched with a control blank. The bandages and patches were removed after six (6) hours of exposure. After a 24 hour rest period, each site was observed on each animal for erythema and edema. This procedure was repeated once a week for three weeks for a total of three applications. Following a two week rest period, the test animals were topically patched with the appropriate test article containing Formula C and the control blank on the control animals. The patches were removed after 6 hours of exposure. The dermal patch sites were observed for crythema and edema at 24, 48 and 72 hours after patch removal. Each animal was assessed for a sensitization response based on dermal observation scores illustrated in Table II.

TABLE II

Dermal Application Observations

| ANIMAL # | 24 Hours ER | 24 Hours ED | 48 Hours ER | 48 Hours ED | 72 Hours ER | 72 Hours ED |
|---|---|---|---|---|---|---|
| TEST GROUP | | | | | | |
| 2078 | 1 | 0 | 0 | 0 | 0 | 0 |
| 2079 | 0 | 0 | 1 | 0 | 1 | 0 |
| 2080 | 0 | 0 | 1 | 0 | 0 | 0 |
| 2081 | 0 | 0 | 0 | 0 | 0 | 0 |
| 2082 | 0 | 0 | 0 | 0 | 0 | 0 |
| 2083 | 0 | 0 | 0 | 0 | 0 | 0 |
| 2084 | 0 | 0 | 1 | 0 | 0 | 0 |
| 2085 | 0 | 0 | 0 | 0 | 0 | 0 |
| 2086 | 0 | 0 | 0 | 0 | 0 | 0 |
| 2087 | 1 | 0 | 0 | 0 | 1 | 0 |
| Total of Scores | 2 | | 3 | | 2 | |
| Severity (Total/10) | 0.2 | | 0.3 | | 0.2 | |
| Incidence % | 20% | | 30% | | 20% | |
| NEGATIVE CONTROL GROUP | | | | | | |
| 2088 | 0 | 0 | 0 | 0 | 0 | 0 |
| 2089 | 0 | 0 | 0 | 0 | 0 | 0 |
| 2090 | 0 | 0 | 0 | 0 | 0 | 0 |
| 2091 | 0 | 0 | 0 | 0 | 0 | 0 |
| 2092 | 0 | 0 | 0 | 0 | 0 | 0 |
| Total of Scores | 0 | 0 | 0 | 0 | 0 | 0 |
| Severity (Total/10) | 0 | 0 | 0 | 0 | 0 | 0 |
| Incidence % | 0% | | 0% | | 0% | |

The application sites were observed for irritation and sensitization reaction, as erythema and edema. The sites were gently wiped with a 70% alcohol soaked prior to each scoring period. The scoring criteria are listed below in Table III.

TABLE III

Dermal Observation Scoring

| ERYTHEMA | EDEMA |
|---|---|
| 0 = No erythema | 0 = No edema |
| 1 = Slight erythema | 1 = Slight edema |
| 2 = Well defined erythema | 2 = Well defined edema |
| 3 = Moderate erythema | 3 = Moderate edema |
| 4 = Severe erythema to slight eschar formation | 4 = Severe edema |

The test results were based upon incidence and severity of the sensitization reaction. Individual animal scores of one (1) or greater in the test group generally indicate sensitization, provided scores of less than one (1) are observed on the control animals. An effect interpreted as "irritation" is generally observed at 24 hours, but diminishes thereafter. The results are summarized in Table IV.

TABLE IV

Irritancy Test results for Formula C

| Test | Results |
|---|---|
| Primary Dermal Irritation | Slight Irritant (Undiluted) |
| Sensitization | Non sensitization |

The results of the test indicate that Formula C has a 20% incidence dermal response with a 0.2 severity index at the 24 hour time point; a 30% incidence with a 0.3 severity index at the 48 hour point; and a 20% incidence with a 0.2 severity index at the 72 hour point. However, the pattern of responses was irregular and did not repeat in every animal from 24 to 48 hours and therefore the response at 24 hours was categorized as an irritation. While a sensitization reaction could not be completely ruled out, Formula C had a slight potential for irritation when applied in semi-occluded conditions and a very low potential for sensitization, it was therefore classified as acceptable in regard to dermal sensitization.

21 Day Cumulative Irritancy and Delayed Challenge Test

The relative skin irritation potential of Formula C solution was compared with three commercially available skin disinfecting formulations (Formulas X, Y and Z). Formulation X is the subject of U.S. Pat. No. 6,090,395 and consists generally of a rinse-less 61% ethanol and 1% CHG solution. Formulation Y is a 4% CHG solution, and Formulation Z, the subject of U.S. Pat. No. 6,110,908, is a brush-free 70% ethanol solution. The formulations were applied to the upper back of twenty-six (26) healthy volunteers daily for twenty-one (21) days, and remained in contact with the skin for twenty-four (24) hours with each application. Dermal irritation was evaluated daily by a dermatologist using the following scoring scale:

0=negative

+=equivocal reaction (0.5)

1=erythema

2=erythema and induration

3=erythema, induration and vesicles

4=bullae

Table V presents the cumulative irritancy scores for the twenty-six (26) healthcare volunteers over the course of the twenty-one (21) day study.

TABLE V

Irritancy scores for 21 Day Cumulative Irritancy Assay and Delayed Challenge

| | Formulation C | Formulation X | Formulation Y | Formulation Z |
|---|---|---|---|---|
| Irritancy Scores | 3 | 47 | 0 | 147 |

Formula C was classified as a "mild material" under occlusive conditions. The irritation score was not different for Formula Y, but significantly less than the patented formulations X and Z.

Sensitization Phase

Formula C and the three commercial test formulations were applied to a naïve site, and irritancy scores were taken at forty-eight (48) and ninety-six (96) hours post application to determine the level of contact sensitization. The scores are presented in Table VI.

TABLE VI

| | Formula C | Formula X | Formula Y | Formula Z |
|---|---|---|---|---|
| Scores | 0 | 4.5 | 0 | 2.5 |

The results of the test again showed that the formulation of the present invention, formula C, had no potential for contact sensitization. The scores in Table VI are the sum of the scores at 48 and 96 hours only.

ANTIMICROBIAL EFFECTIVENESS TEST

In Vitro Antimicrobial Efficacy of Formula C

The efficacy of Formula C as an antimicrobial formulation was tested at 70% ethyl alcohol. The study evaluated the effectiveness of Formula C solution as a surgical scrub and hand antiseptic against broad-spectrum microorganisms. The study brought into contact Formula C with a population of organisms for a specific period of time at a specific temperature. The organisms included gram positive and gram negative bacteria, yeast, and molds that are commonly implicated in surgical wound infections. The percent reduction from the initial population was calculated for each of the organisms. The population reduction is presented in Table VII.

TABLE VII

In-vitro Time Kill Study at Full Strength (Log Reduction)

| | Formula C | Formula D | Formula F | Formula G | Formula X | Formula Z |
|---|---|---|---|---|---|---|
| Gram: Positive Bacteria | | | | | | |
| *Staphylococcus aureus* | | | | | | |
| 15 seconds | >6 log | >6 log | >6 log | >6 log | >5 log | >4 log |
| 30 seconds | >6 log | >6 log | >6 log | >6 log | >5 log | >4 log |
| *Staphylococcus epidermidis* | | | | | | |
| 15 seconds | >6 log | >6 log | >6 log | >6 log | >6 log | >4 log |
| 30 seconds | >6 log | >6 log | >6 log | >6 log | >6 log | >4 log |
| Gram: negative bacteria | | | | | | |
| *Enterococcus faecalis* | | | | | | |
| 15 seconds | >6 log | >6 log | >6 log | >6 log | >6 log | >4 log |
| 30 seconds | >6 log | >6 log | >6 log | >6 log | >6 log | >4 log |
| *Escherichia coli* | | | | | | |
| 15 seconds | >6 log | >6 log | >6 log | >6 log | >6 log | >3 log |
| 30 seconds | >6 log | >6 log | >6 log | >6 log | >6 log | >3 log |
| *Enterobacter cloacae* | | | | | | |
| 15 seconds | >6 log | >6 log | >6 log | >6 log | >6 log | >4 log |
| 30 seconds | >6 log | >6 log | >6 log | >6 log | >6 log | >4 log |
| *Pseudomonas aeruginosa* | | | | | | |
| 15 seconds | >6 log | >6 log | >6 log | >6 log | >6 log | >4 log |
| 30 seconds | >6 log | >6 log | >6 log | >6 log | >6 log | >4 log |
| *Proteus vulgaris* | | | | | | |
| 15 seconds | >6 log | >6 log | >6 log | >6 log | >6 log | >4 log |
| 30 seconds | >6 log | >6 log | >6 log | >6 log | >6 log | >4 log |
| *Klebsialla pneumoniae* | | | | | | |
| 15 seconds | >6 log | >6 log | >6 log | >6 log | >6 log | >4 log |
| 30 seconds | >6 log | >6 log | >6 log | >6 log | >6 log | >4 log |
| *Serratia marcescens* | | | | | | |
| 15 seconds | >6 log | >6 log | >6 log | >6 log | >6 log | >4 log |
| 30 seconds | >6 log | >6 log | >6 log | >6 log | >6 log | >4 log |
| Yeast | | | | | | |
| *Candida albicans* | | | | | | |
| 15 seconds | >6 log | >6 log | >6 log | >6 log | >6 log | >4 log |
| 30 seconds | >6 log | >6 log | >6 log | >6 log | >6 log | >4 log |

Formulations C, D, F, and G, of the present invention, with moisturizer provided rapid antimicrobial kill of broad-spectrum microorganisms with greater than log 6 microbial kill in 15 seconds. In comparison, the patented formulations X (U.S. Pat. No. 6,090,395) and Z (U.S. Pat. No. 6,110,908) provided less effective kill rates depending on the species of bacteria examined. The present invention showed an uncommon effectiveness against one of the more deleterious *Staphylococcus* strains, *Staphylococcus aureus*. All formulations of the present invention had a greater than log 6 reduction of *Staphylococcus aureus*, while Formula X managed a log reduction of greater than 5, an order of magnitude less effective and formula Z was less effective by two orders of magnitude having a log reduction of greater than 4.

In Vitro Minimum Inhibitory Concentration, Formula C of the Present Invention

In another study the minimum inhibitory concentration of Formula C was investigated. Formula C was used as the (test solution), and 70% ethyl alcohol solution as the (control solution) were diluted with a trypticase soy broth microbial growth media. Subsequent dilutions had the concentration calculated in ppm. Each concentration was challenged with an equal volume of microbial inoculums. After incubation the lowest concentration showing "No-Growth" was recorded as the Minimum Inhibitory Concentration. At full strength both Formula C and a 70% ethyl alcohol solution contain 70,000 ppm.

TABLE VIII

Minimum Concentrations of Formula C and 70% Ethyl Alcohol to Exhibit Antimicrobial Activity

| Organisms | ATCC or CI* | Formula C | 70% ethyl alcohol |
|---|---|---|---|
| *Acinetobacter baumannii* | 19606 | 182 ppm | 4375 ppm |
| *Acinetobacter baumannii* | 061901Ab1* | 273 ppm | 8750 ppm |
| *Bacteroides fragilis* | 25285 | 273 ppm | 8750 ppm |
| *Bacteroides fragilis* | 061901Bf2* | 547 ppm | 8750 ppm |
| *Candida albicans* | 10231 | 1094 ppm | 17500 ppm |
| *Candida albicans* | 040400Ca2* | 1094 ppm | 17500 ppm |
| *Candida tropicalis* | 750 | 1094 ppm | 17500 ppm |
| *Candida parapsilosis* | 040400Cp2* | 1094 ppm | 17500 ppm |
| *Enterobacter aerogenes* | 13048 | 547 ppm | 8750 ppm |
| *Enterobacter acrogenes* | 040400Ea1* | 182 ppm | 8750 ppm |
| *Enterococcus faecalis* | 29212 | 273 ppm | 8750 ppm |
| *Enterococcus faecalis* | 040400Esp17* | 273 ppm | 8750 ppm |
| *Enterococcus faecium* | 51559 | 183 ppm | 8750 ppm |
| *Enterococcus faecium* | 061901Efm1* | 273 ppm | 8750 ppm |
| *Escherichia coli* | 11229 | 91 ppm | 8750 ppm |
| *Escherichia coli* | 051599Ec* | 68 ppm | 8750 ppm |
| *Escherichia coli* | 25922 | 68 ppm | 8750 ppm |
| *Escherichia coli* | 070399Ec* | 137 ppm | 8750 ppm |
| *Haemophilus influenzae* | 19418 | 183 ppm | 5833 ppm |
| *Haemophilus influenzae* | 121699Hi* | 46 ppm | 5833 ppm |
| *Klebsiella oxytoca* | 43165 | 183 ppm | 8750 ppm |
| *Klebsiella oxytoca* | 061901Ko1* | 183 ppm | 8750 ppm |
| *Klebsiella pneumoniae* | 13883 | 68 ppm | 4375 ppm |
| *Klebsiella pneumoniae* | 06190Kpnl* | 137 ppm | 8750 ppm |
| *Micrococcus luteus* | 7468 | 17 ppm | 8750 ppm |

CI*-Clinical isolate

The data from Table VIII clearly illustrates that Formula C inhibits bacteria growth at a lower concentration than a 70% ethyl alcohol solution. The greater than fifteen fold growth inhibition activity of Formula C is largely attributable to the cocktail of antimicrobial agents used as preservatives.

In Vivo Antimicrobial Efficacy

Formula C was tested under the US Food and Drug Administration Tentative Final Monograph (TFM) for *Effectiveness Testing of a Surgical Hand Scrub*. This study evaluates the antimicrobial efficacy of one (1) test product and three (3) reference products for use as surgical scrubs. The procedure followed is described in the TFM for Pre-surgical Scrub Preparations (FR 59 [116], Jun. 17, 1994: pp. 31455–31448), with the objective of determining whether the test products would satisfy the critical indices of the TFM, such as:

An immediate one (1) $\log_{10}$ reduction in microorganisms on Day 1;

An immediate two (2) $\log_{10}$ reduction in microorganisms on Day 2;

An immediate three (3) $\log_{10}$ reduction in microorganisms on Day 5;

And that microbial counts from the samples taken approximately three (3) hours to three (3) hours and thirty (30) minutes AND approximately six (6) hours to six (6) hours and thirty (30) minutes post-scrub not exceed the baseline counts.

The study was conducted to evaluate the antimicrobial effectiveness of Formula C solution compared to Formulas X and Z, and a combination of Formula C with 4% CHG. The results are presented in Table IX.

TABLE IX

FDA Approved Hand Scrub Efficacy Test

| Immediate Log Reduction | Formula C | Formula C with 4% CHG | Formula X | Formula Z |
|---|---|---|---|---|
| Day 1 | 1.76 | 2.07 | 1.63 | 0.35 |
| Day 2 | 2.31 | 2.98 | 2.22 | 1.21 |
| Day 3 | 3.03 | 3.47 | 2.52 | 2.75 |

The Comparative antimicrobial efficacy test data presented in Table IX, tested four different surgical hand scrubs. The data is reported as the immediate log reduction in microbial counts per hand when sampled one minute following the daily scrub over a five day period. Log reduction relates to a 10-fold or one decimal or 90% reduction in numbers of recoverable bacteria in a test food vehicle, that is a 1 log reduction would reduce the number of bacterias 90%. This means, for example, that 100 bacteria would be reduced to 10 or 10 reduced to 1. Table X represents the percent reduction of bacteria for logs one through five.

TABLE X

Microbial Log Reduction
Log Reduction Chart

| Log Reduction | % Reduction of Bacteria |
|---|---|
| 1 | 90 |
| 2 | 99 |
| 3 | 99.9 |
| 4 | 99.99 |
| 5 | 99.999 |

Formula C produced significant immediate log reduction 1.76 on test day 1, 2.31 on test day 2 and 3.03 on test day five (5). The microorganism population from the Formula C sample, was day six and a half (6.5)hours following the scrub innoculation, and did not return to pre-scrub microbial baseline levels. This data indicates that Formula C met the criteria indices of the DA Tentative Final Monograph for a surgical scrub. The test data also confirmed that the integrated product of Formula C and 4% CHG is the best practice for a surgical scrub. The integrated products produced significant immediate log reduction 2.07 on test day 1, 2.98 on test day 2 and 3.47 on test day 5. The test data also indicates that Formula X (U.S. Pat. No. 6,090,395) and Formula Z (U.S. Pat. No. 6,110,908) did not meet the criteria indices of the FDA as specified in the Tentative Final Monograph for a surgical scrub product.

It will be apparent that the present invention has been described herein with reference to certain preferred or exemplary embodiments. The preferred or exemplary embodiments described herein may be modified, changed, added to, or deviated from without departing from the intent, spirit and scope of the present invention.

What is claimed is:

1. An antimicrobial composition comprising:
    a) an alcohol in an amount from about 60 to about 95 weight percent of the total composition;
    b) a preservative in an amount from about 0.001 to about 5.0 weight percent of the total composition;
    c) a thickening agent in an amount from about 0.01 to about 3 weight percent of the total composition wherein said thickening agent is a cationic cellulose polymer;
    d) a moisturizer and/or emollient in an amount from about 0.005 to about 5.0 weight percent of the total composition;
    e) a cationic emulsifier in an amount from about 0.01 to about 3 weight percent of the total composition
    f) water in an amount from about 6 to about 30 weight percent.

2. The composition of claim 1 wherein the cationic emulsifier is a cationic quaternary ammonium salt.

3. The composition of claim 1 wherein the alcohol is selected from the group consisting of ethyl alcohol, isopropyl alcohol, n-propyl alcohol and mixtures thereof.

4. The composition of claim 1 wherein the preservative is a mixture of benzethonium chloride in an amount from about 0.02 to about 1.0 percent by weight, benzalkonium chloride in an amount from about 0.02 to about 1.0 percent by weight, and chlorhexidine gluconate in an amount from about 0.01 to about 2.0 percent by weight.

5. The composition of claim 1 which additionally contains an effective amount of diazolidinyl urea and 3-Iodo-propynylbutylcarbamate.

6. The composition of claim 5 wherein the total amount of diazolidinyl urea and 3-Iodo-propynylbutylcarbamate is from about 0.05 to about 0.5 percent by weight.

7. The composition of claim 5 which additionally contains an effective amount of methyl paraben, propyl paraben, and propylene glycol.

8. The composition of claim 7 wherein the total amount of diazolindinyl urea, methyl paraben, propyl paraben, and propylene glycol is from about 0.05 to about 2.0 percent by weight.

9. A method of disinfecting a substrate comprising the step of applying to the substrate an effective amount of the antimicrobial composition of claim 1.

10. The method of claim 9 wherein the substrate is a hand.

11. The method of claim 9 further comprising the step of applying an antimicrobial formulation of alcohol to the substrate.

12. The composition of claim 1 wherein the preservative is one or more of the compounds selected from the group consisting of parachlorometaxylenol, phenoxy ethanol, benzalkonium chloride, benzethonium chloride, chlorhexidine gluconate, chlorhexidine diacetate, hexetidine, and triclosan.

13. The composition of claim 1 wherein said moisturizer and/or emollient is one or more of the compounds selected from the group consisting of mineral oil, dimethicone, glycerin, isopropyl palmitate, propylene glycol, petrolatum, and squalane.

14. An antimicrobial composition comprising:
    a) an alcohol in an amount from about 60 to about 95 weight percent of the total composition;
    b) a preservative in an amount from about 0.001 to about 5.0 weight percent of the total composition wherein said preservative is one or more of the compounds selected from the group consisting of parachlorometaxylenol, phenoxy ethanol, benzalkonium chloride, benzethonium chloride, chlorhexidine gluconate, chlorhexidine diacetate, hexetidine, and triclosan;
    c) a thickening agent in an amount from about 0.01 to about 3 weight percent of the total composition wherein said thickening agent is a cationic cellulose polymer;
    d) a cationic emulsifier in an amount from about 0.01 to about 3 weight percent of the total composition;
    e) a moisturizer and/or emollient in an amount from about 0.005 to about 5.0 weight percent of the total composition wherein said moisturizer and/or emollient is one or more of the compounds selected from the group consisting of mineral oil, dimethicone, glycerin, isopropyl palmitate, propylene glycol, petrolatum, and squalane; and
    f) water in an amount from about 6 to about 30 weight percent.

15. The composition of claim 14 wherein the cationic emulsifier is a cationic quaternary ammonium salt.

16. The composition of claim 14 wherein the alcohol is selected from the group consisting of ethyl alcohol, isopropyl alcohol, n-propyl alcohol and mixtures thereof.

17. The composition of claim 14 wherein the preservative is a mixture of benzethonium chloride in an amount from about 0.02 to about 1.0 percent by weight, benzalkonium chloride in an amount from about 0.02 to about 1.0 percent by weight, and chlorhexidine gluconate in an amount from about 0.01 to about 2.0 percent by weight.

18. The composition of claim 14 which additionally contains an effective amount of diazolidinyl urea and 3-Iodo-propynylbutylcarbamate.

19. The composition of claim 18 wherein the total amount of diazolidinyl urea and 3-Iodo-propynylbutylcarbamate is from about 0.05 to about 0.5 percent by weight.

20. The composition of claim 19 which additionally contains an effective amount of methyl paraben, propyl paraben, and propylene glycol.

21. The composition of claim 20 wherein the total amount of diazolidinyl urea, methyl paraben, propyl paraben, and propylene glycol is from about 0.05 to about 2.0 percent by weight.

22. A method of disinfecting a substrate comprising the step of applying to the substrate an effective amount of the antimicrobial composition of claim 14.

23. The method of claim 22 wherein the substrate is a hand.

24. The method of claim 22 further comprising the step of applying a solution of chlorhexidine gluconate.

25. The composition of claim 14 which additionally contains a fragrance.

26. The composition claim 14 which additionally contains a colorant.

* * * * *